United States Patent [19]

Richards

[11] 4,014,320
[45] Mar. 29, 1977

[54] AUDIOMETRIC APPARATUS

[76] Inventor: George Benton Richards, 804 Harmon, Longview, Tex. 75601

[22] Filed: May 14, 1975

[21] Appl. No.: 577,451

[52] U.S. Cl. .................................. 128/2 Z; 128/2 F
[51] Int. Cl.² ........................................ A61B 5/12
[58] Field of Search .......... 128/2 R, 2 K, 2 M, 2 Z, 128/231, 233, 246, 349 B; 179/1 N, 182 R, 182 A; 181/129, 130, 132, 133, 134, 135; 73/67.1, 69

[56] References Cited

UNITED STATES PATENTS

| | | | |
|---|---|---|---|
| 2,781,416 | 2/1957 | Brogan | 179/1 N |
| 3,272,926 | 9/1966 | Falkenberg | 179/182 R |
| 3,408,658 | 11/1968 | Beguin | 179/182 R X |
| 3,469,651 | 9/1969 | Mendelson | 181/135 |
| 3,707,146 | 12/1972 | Cook | 128/2 R |
| 3,757,769 | 9/1973 | Arguimbau | 128/2 Z |

FOREIGN PATENTS OR APPLICATIONS 917,143  8/1954  Germany .......................... 128/2 Z

OTHER PUBLICATIONS

M. B. Kruk et al., "Instrument for Determining the Patency of the Eustachian Tube", Biomed., Eng. (USA) vol. 6, No. 1 (Jan., Feb., 1972) pp. 50–51.

*Primary Examiner*—Harland S. Skogquist
*Attorney, Agent, or Firm*—Arnold, White & Durkee

[57] ABSTRACT

A pair of probes insertable into both auditory canals of a patient are provided, each probe carrying a readily replaceable, inflatable bladder for sealingly positioning the probes. A trio of conduits terminate at a disc at an end of each probe to provide audio stimulus, audio detection and air pressure control. Transducers coupled to sound transmitting conduits are carried in a pair of housings mounted on a frame which supports the axially and radially adjustable probes.

2 Claims, 6 Drawing Figures

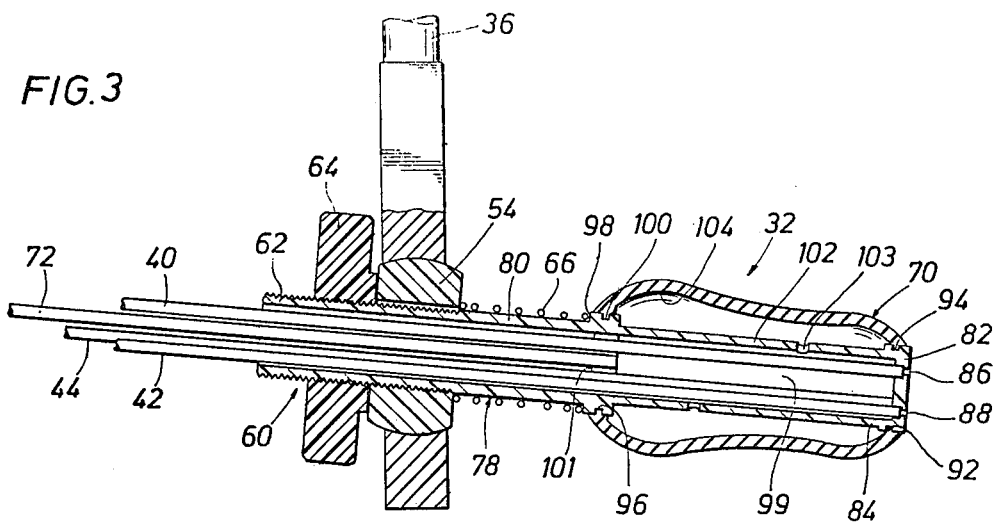
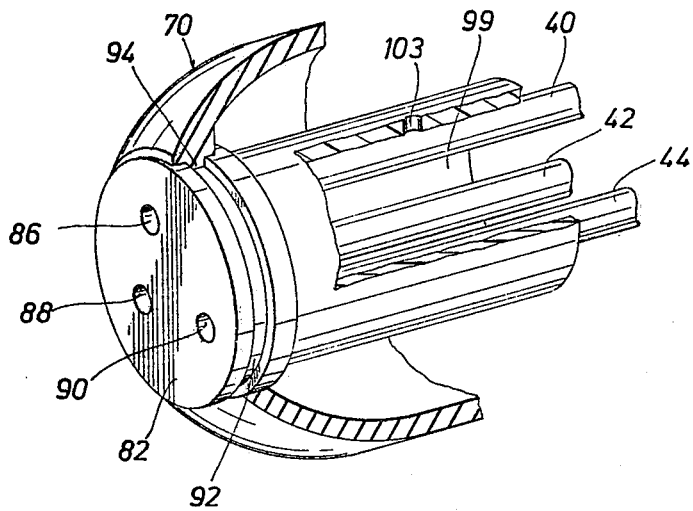
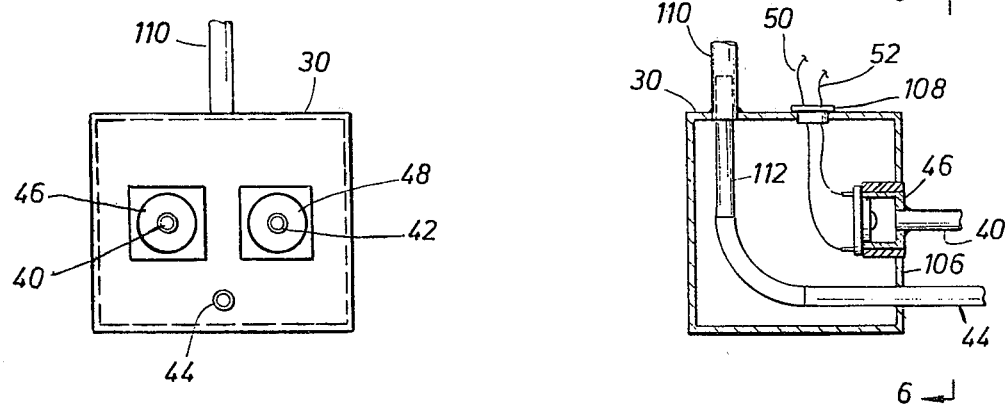

AUDIOMETRIC APPARATUS

BACKGROUND OF THE INVENTION

This invention relates generally to a novel audiometric device.

More particularly, this invention concerns an apparatus useful in performing contralateral testing of intraaural muscle reflex. Whereas a wide variety of audiometric tests may be conducted with the apparatus of the present invention, the apparatus will find particular utility in rapid sequenced contralateral testing of intraaural muscle reflex.

In the past it has been useful for a physician or audiologist to measure various acoustic parameters of a patient's ear in order to diagnose ear malfunctions. Inasmuch as many ear malfunctions occur in the middle ear and cannot be observed directly by the physician or audiologist, different tests must be performed in order to isolate and identify the most probable cause of a hearing or ear malfunction.

Because of the relatively small dimensions and location of the critical hearing components of the ear, the testing procedures must necessarily be conducted with a minimum of error. In addition, the testing procedure desirably imposes minimal discomfort on the patient being tested. This latter aspect needs attention lest people are discouraged from submitting to such testing voluntarily.

In accoustic impedance audiometry, a contralateral testing method has been established as an indicator of hearing function. In this test, the external auditory meatus or canal of one ear is penetrated by a probe. This probe is then sealed off from the ambient atmosphere to isolate a volume lying between the probe tip and the tympanic membrane or eardrum. By controlling the pressure within this isolated volume, the eardrum may be manipulated to a neutral position. In this position of the eardrum, a known condition is achieved in the stapedius muscle and in the tensor-tympani muscle. In normal cases, the eardrum is a compliant condition in a neutral position.

As this test has been conducted in the prior art, the opposite ear is covered with an audiometric headset of the type disclosed in the U.S. Pat. No. 3,220,505 to Hargrave in order to present a closely controlled sound stimulus to that other ear. When the other ear is stimulated with sound, a response occurs in the probed ear. This response is in the nature of muscle reflex of the stapedius muscle, and, in some cases, of the tensor-tympani muscle, and this reflex results in a movement of the eardrum. This movement of the eardrum may be detected as a pressure change or as a geometric change in the probed ear. This intraaural muscle reflex which occurs in one ear as a result of a stimulus in the other ear occurs by virtue of a phenomenon of neural crossover. This reflex is useful to a physician or audiologist in determining hearing functions particularly in patients who are unable to communicate to the examiner the presence of an audible tone, e.g., infants or handicapped persons.

The probe tip and headset utilized in tests in the past are required to be very carefully positioned with respect to the patient's ears. This careful placement is necessitated by the precise nature of the examination. The positioning of this equipment may be extremely time consuming and, hence, limit the number of patients which may be examined by a physician or audiologist in a given time period. Moreover, it will be appreciated that when it is desired to test the intraaural muscle reflex of the other ear, the equipment must be reversed. That is, the probe must be removed from the first ear and repositioned in the second ear, and the headset must be positioned on the opposite ear.

Of related significance is the ease with which a probe may be inserted and held in position in the auditory canal of a patient. It will, of course, be appreciated that in the performance of various audiological tests, the probe tip must be sealed in such a manner as to permit the isolation of a volume between the probe tip and the ear drum. In the past, earplugs and ear probes have been available with a flexible, expandable bag or bladder adapted for expansion within the auditory canal of the ear. After the probe has been inserted into the auditory canal to a desired depth, the bladder of the expandable bag is inflated or pressurized. Such probe tips represent a relatively fast way of sealing a probe in an auditory canal. However, inasmuch as these probe tips must be cleaned between use, it has been found that the bladders do not inflate satisfactorily or give as desirable a seal after repeated cleanings.

Recognizing the need for an improved audiometric device for contralateral intraaural muscle reflex testing, it would therefore be desirable to provide an audiometric apparatus which eliminates the necessity of moving the testing apparatus from one ear to another and wherein such apparatus provides quick sealing ear probe tips which are readily replaceable and sufficiently inexpensive in cost to be disposed of after use.

OBJECTS AND SUMMARY OF A PREFERRED EMBODIMENT OF THE INVENTION

It is, therefore, a general object of the present invention to provide a novel audiometric device which minimizes or reduces the problems of the type previously noted.

It is a more particular object of the present invention to provide a novel audiometric device which facilitates administering relatively fast and accurate sequenced contralateral testing of intraaural muscular reflex.

Yet another object of the present invention is to provide a novel audiometric device having probes with tips which may be quickly adjusted to provide a consistently satisfactory seal between the auditory canal and the ambient atmosphere.

One feature of the audiometric apparatus of the present invention is in one embodiment, a disposable, inflatable probe tip. Another feature of the audiometric apparatus of the present invention is a pair of ear probes operably arranged for infinite axial and radial alignment in a patient's ears. Still another feature of the apparatus of the present invention is a capability for testing intraaural muscle reflex without necessitating the removal of a probe from one ear and insertion of the probe into the other ear accompanied by a removal of a muff type ear phone from one ear to the other.

An audiometric device according to a preferred embodiment of the invention intended to substantially accomplish the foregoing objects and having the foregoing features includes a first probe tip for isolating from ambient conditions a first auditory canal of a patient and a second probe tip for isolating from ambient conditions the other auditory canal of the patient. A first audio generator is provided for generating an audio stimulus to the first auditory canal and a second audio generator is provided for producing an audio stimulus to the second auditory canal. A response detector is also provided for each of the probe tips in order to detect a response in the first and the second auditory canals to the stimulus produced by the corresponding audio generator.

The probe may carry a generally hourglass shaped probe tip which may be inflated once the probe has been inserted to a desired depth in the auditory canal of the patient. The probe itself is mounted for essentially unlimited or infinite axial and radial alignment within a range as the probe is inserted into the auditory canal. A carriage or frame arrangement is provided which permits the patient's head to support the probes and to facilitate locking the probe into its final position for conducting an audiological test.

Examples of the more important features of this invention have thus been given in rather broad terms in order that the detailed description thereof that follows may be better understood, and in order that the contribution to the art may be better appreciated. There are, of course, additional features of the invention that will be described hereinafter and which will also form the subject of the claims appended hereto.

Other objects, advantages and features of the present invention will become apparent with reference to the following detailed description of a preferred embodiment thereof in connection with the accompanying drawings wherein like reference numerals have been applied to like elements, in which:

BRIEF DESCRIPTION OF THE DRAWINGS

FIG. 3 is a partial sectional view which depicts in greater detail a probe and probe tip of the apparatus shown in FIG. 1;

FIG. 4 is a more detailed partial sectional view of the probe and probe tip of the apparatus illustrated in FIG. 3;

FIG. 5 is a partial sectional view of a transducer and transducer housing which is carried by the apparatus shown in FIG. 1; and FIG. 6 is a partial sectional view taken along section lines 6 — 6 in FIG. 5.

DETAILED DESCRIPTION OF A PREFERRED EMBODIMENT OF THE INVENTION

Figure 1:
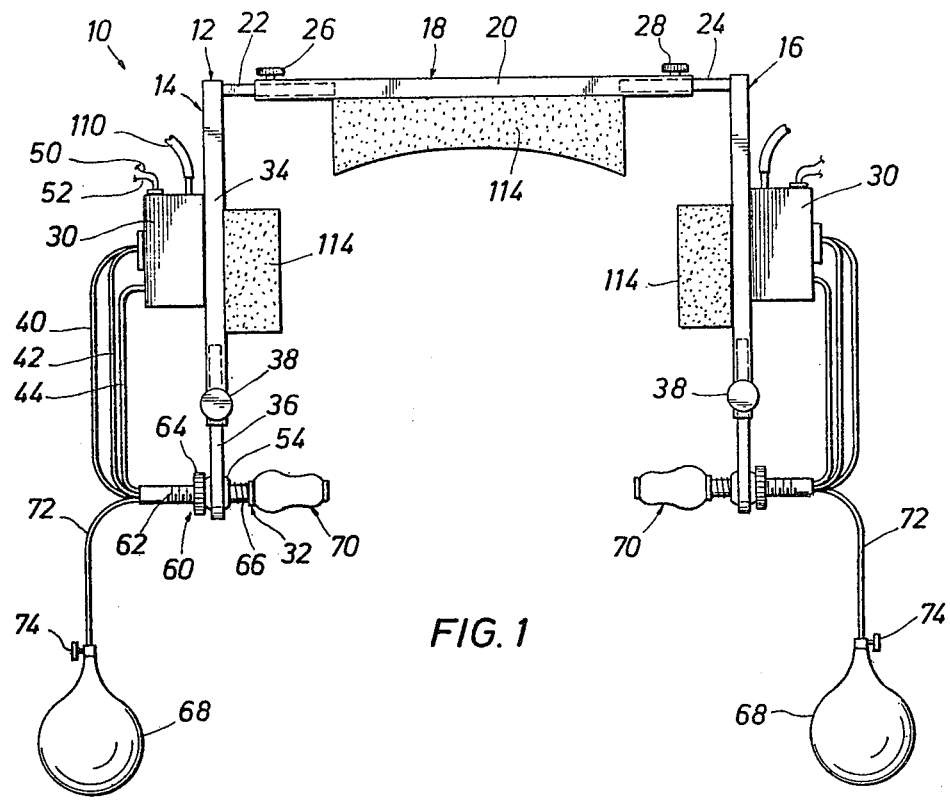
FIG. 1 schematically depicts an audiometric device of the present invention having a frame, a pair of transducer housings and a pair of generally hourglass shaped probe tips overlying the probes.

Turning first to FIG. 1, there may be seen an audiometric headset 10 according to the present invention. The headset comprises a frame or carriage 12 including a pair of vertical portions 14, 16 and a horizontal portion 18. The horizontal portion 18 includes a bracing member 20 into which there is telescopingly inserted a left horizontal slide rod 22 and right horizontal slide rod 24. A set screw 26 is threaded into the bracing member 20 to lock the left horizontal slide rod 22 into place. Similarly another set screw 28 is provided for locking the right horizontal slide rod 24 into a desired position.

With respect to the vertical portions of the frame, it may be seen in FIG. 1 that the left and the right portions 14 and 16 are mirror images. Therefore, a description of one side would in fact describe both.

The left vertical portion 14 carries a transducer housing 30 and an auditory canal probe 32. The transducer housing 30 is attached to a left bracing member 34 which is attached to the left horizontal slide rod 22. A left vertical slide rod 36 is telescopingly inserted into the left vertical bracing member 34 and a set screw 38 may be threaded into the bracing member to lock the vertical slide rod 36 in a desired position. Three conduits 40, 42, 44 extend from the transducer housing 30 to the probe 32. Of course it will be appreciated that these conduits may be included in a single cable or other such similar arrangement. These conduits include an air pressure conduit or tube 44 and a pair of transducer coupling conduits or tubes 40, 42. Transducer coupling tubes 40, 42 place the probe 32 in communication with an audio stimulus producing transducer or "send" transducer 46 and an audio response detecting transducer or microphone which may be referred to as a "receive" transducer 48 (see FIGS. 5 and 6).

The transducers 46, 48 contained within the transducer housing 30 are conventional miniature transducers or microtransducers and are adaptable for interconnection through electric cables 50, 52 to the appropriate test equipment (not shown). It will be appreciated that the inside diameter of each of the transducer coupling tubes 40, 42 which couple the transducers to the probe is calculated to minimize undesirable audiological effects.

The probe 32 is mounted for pivotal movement about a coupling 54 to facilitate insertion of the probe into auditory canals of varying geometries. It will be appreciated that the probe 32 may be moved to an essentially infinite number of positions within the limits or range of travel of the coupling 54. This arrangement facilitates an angular orientation of the probe 32 in order to correspond to an auditory canal 56 of a patient 58 (see FIG. 2).

In addition, the probe is movable axially by a probe depth adjustment mechanism 60 comprising a threaded portion 62 which may be moved axially by manipulation of a thumb wheel 64. A spring 66 may be used to maintain the probe in a desired axial position (see FIG. 3). This arrangement enables the physician or audiologist to position the probe in the auditory canal at an appropriate location to conduct contralateral testing.

As will be explained more fully below, after the probe 32 has been positioned in the auditory canal 56 of the patient 58 (see FIG. 2), a pump bulb 68 may be manually actuated to inflate a gum rubber probe tip 70. This pump bulb 68 is placed in communication with the probe tip through a probe tip inflation conduit 72, and a thumb-screw operated pressure release valve 74 on the pump bulb is operable to release pressure when it is desired to deflate the gum rubber probe tip 70.

Figure 2:
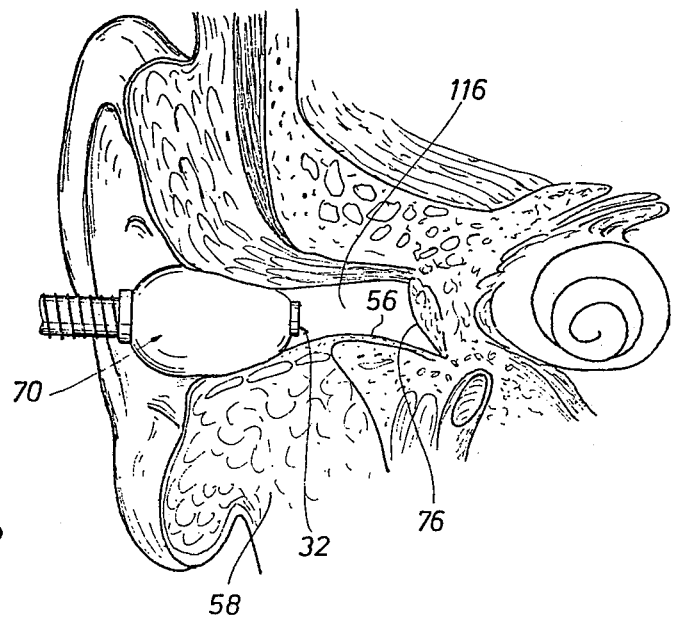
FIG. 2 is a partial sectional view of an ear of a patient with a probe of the apparatus of FIG. 1 inserted into the auditory canal with the probe tip inflated to isolate from ambient conditions a volume between the probe tip and the eardrum of the patient.

As may be seen in FIG. 2, after the probe has been inserted to a desired depth in the auditory canal 56, the probe tip 70 is inflated to seal off a chamber 116 between the probe 32 and an eardrum or tympanic membrane 76 of the patient 58. The probe tip 70 expands to conform to the walls of the auditory canal 56 and to substantially axially center the probe 32 in the auditory canal 56.

As may be seen in FIG. 3, the probe 32 includes a rigid jacket 78 having a smooth portion 80 and the threaded portion 62. A perforated disc 82 is attached to or integrally formed with an end 84 of the smooth portion of the jacket 78. As may be seen in FIG. 4, this disc 82 has three perforations 86, 88, 90, one perforation 90 being adapted to receive an end of the air pressure tube 44, one perforation 86 being adapted to receive an end of the send transducer tube 40, and the remaining perforation 88 being adapted to receive an end of the receive transducer tube 42.

A first groove or channel 92 is provided around the circumference of the disc 82. This first channel 92 is adapted to receive an annular flange 94 on the inflatable gum rubber probe tip 70 (see FIG. 4). Similarly, a second channel 96 is provided around the jacket 78. A wall 98 of the second channel forming member is operable to limit the travel of the spring 66 (see FIG. 3). This second channel 96 similarly receives a flange 100 at another end of the inflatable gum rubber probe tip 70.

A seal 101 is provided to isolate the interior 99 of an end portion 102 of the jacket from the atmosphere. At least one aperture 103 is provided in the end portion 102 of the jacket 78 to provide fluid communication between the interior 99 of the end of the jacket and the flexible probe tip 70. Thus it will be appreciated that when the first flange 94 and the second flange 100 are seated in the respective channels 92 and 96, a substantially fluid tight seal is provided between the interior 99 of the end portion 102 of the jacket 78 and an interior wall 104 of the inflatable gum rubber probe tip.

The pump bulb inflation tube 72 is placed in communication with the interior portion 99 of the jacket to enable the probe tip 70 to become inflated.

The inflatable tip 70 of the probe 32 is essentially hourglass shaped at ambient pressures, but, as may be seen in FIG. 2, when inflated, this probe tip assumes a shape to conform to the wall of the auditory canal 56. It will be appreciated that the probe tip 70 may be stretched slightly to pass over the perforated disc 82 so that the probe tip may be positioned over the end portion 102. The probe tip may then be stretched slightly to bring the flanges 94 and 100 into cooperation with the grooves or channels 92 and 96 on the probe. The attachment of the probe tip 70 to the probe 32 is a relatively simple operation which may be performed quickly thereby facilitating the use of disposable gum rubber probe tips.

It will of course be appreciated that other arrangements may be used in sealing the probe tip 70 to the probe 32. For example, an essentially hourglass shaped probe tip may be applied to the probe but without flanges. In such an arrangement, it may be desirable to utilize a garter spring of some kind to urge the proximal and distal ends of the probe tip into the grooves or channels in the probe. Also, probe tips having geometries other than a generally hourglass configuration may be used with the apparatus of the present invention. However, it has been found, that the hourglass configuration permits the probe to be smoothly inserted into the auditory canal of a patient, moved into position, and inflated to seal the probe in a patient's auditory canal in a relatively fast and effortless operation. It is contemplated, however, that within the scope of this invention, probe tips other than the inflatable types disclosed herein may be used. For example, a flexible but noninflating generally cone shaped probe may be used.

In FIGS. 5 and 6 there may be seen two cutaway or sectional views of the transducer housing 30 shown in FIG. 1. The send transducer 46 and the receive transducer 48 may be mounted on a wall 106 of the transducer housing through any conventional means. The transducer housing tends to insulate the transducers from spurious sound and facilitate the careful parametric control of the transducers. The electrical conduits 50 and 52 leading to the transducers 46 and 48 pass through a grommet 108 in an upper wall of the transducer housing. The send and receive transducer coupling tubes 40 and 42 are conventionally attached to the transducers 46 and 48 An air pump input hose 110 is attached to an air transport tube or conduit 112 which passes through the interior of the transducer housing. It will be appreciated that the transducer housing serves as a convenient terminal for the air pressure conduits 110 and 44 and that these conduits may be introduced into the probe 32 through other means.

In operation, the headset may be placed across the top of a patient's head in the now well-known manner. Foam pads 114 countoured to accommodate the head are provided to facilitate comfortable placement of the apparatus on a patient's head. The horizontal bracing member 20 is approximately centered tangentially to the vertex of the patient's head. The left and right vertical adjustment rods 36 may then be adjusted to the appropriate level for insertion of the probe 32 into the auditory canals 56 of the patient. The left and right horizontal slide rods 22 and 24 may be moved inboard or outboard to effectuate penetration of the probes into the auditory canals. The probe depth adjustment screw 64 may then be adjusted for a finer positioning of the probe 32 in the auditory canal. After the probe has been positioned, the pump bulb venting thumb screw 74 is moved to a closed position and the bulb 68 is manually pumped to inflate the probe tip 70. As shown in FIG. 2, the probe tip 70 inflates to conform to the walls of the auditory canal, and a closed chamber 116 is formed which is defined by the walls of the auditory canal 56, the eardrum 76, and the probe 32. The pressure of this chamber 116 may be controlled and monitored by means of the air pressure conduit 44 running through the probe and to the test equipment (not shown).

In contralateral testing, the eardrum 76 of the ear wherein the intraaural muscle reflex is to be tested is brought to an equilibrium position by adjusting the pressure in the chamber 116 between the probe and the eardrum to approximately the same pressure existing in the middle ear through a procedure known in the art. In this equilibrium state, the eardrum 76 is compliant, and if the stapedius muscle (and in some cases the tensortympani muscle) flexes, a movement of the eardrum will be reflected as a change in the pressure in the chamber 116 between the probe 32 and the eardrum 76. Clearly, as the volume of that chamber 116 decreases by virtue of the eardrum 76 moving towards the probe 32, the pressure in that chamber will increase, and vice versa.

With both ears probed in accordance with the present invention, contralateral testing of intraaural muscle reflex may be conducted by first stimulating, say, the right ear with an audible tone and monitoring in response thereto any change in volume of the chamber 116 provided in the left ear. In the prior art, this known stimulus was introduced by means of a muff type earphone. The other ear (that is, the ear not covered by the muff type earphone) was probed in order to monitor eardrum movement. According to the present invention, both ears of the patient are probed. The send transducer 46 is operable as a tone stimulus source. Because the stimulus tone is emanated from a source essentially within the auditory canal 56, much greater control may be maintained over those parametric variables which directly affect the accuracy of audiological testing. That is, the stimulus tone is presented at a location much closer to the eardrum than with prior art devices used for this test and losses may be more readily compensated for at such a location.

In a known procedure for testing contralateral intraaural muscle reflex, the pressure in the chamber 116 defined by the probe 32 and the eardrum 76 is continuously controlled. This control is effected by first making a comparison of the acoustic condition in the chamber 116 when the eardrum is in a compliant and then in a noncompliant condition. The eardrum may be made noncompliant by the application of pressure which causes the eardrum to stretch. In such a condition, a first set of parametric conditions exist within the chamber 116. By the reduction of pressure within the chamber, the eardrum may be permitted to relax and to move towards a neutral position or a position of maximum compliance. A second set of parametric conditions exist within the chamber 116 when the eardrum is in a condition of maximum compliance. It is in this condition of maximum compliance that intraaural muscle reflex is most easily determined. In order to maintain the eardrum in this most compliant condition, a tone is introduced into the chamber by the send transducer 46 and the acoustical response to this stimulation is then monitored by the receive transducer 48. If the audiological parameters in the chamber 116 indicate that the eardrum has moved away from its position of maximum compliance, the pressure in the chamber is adjusted accordingly by means of conduit 44 to bring the eardrum back to its most relaxed condition.

With the apparatus of the present invention, sequenced contralateral testing may be conducted. First, one ear is stimulated for response in the opposite ear, and then the opposite ear is stimulated for response in the first ear. This complete test may be conducted without having to move a probe from one ear to another.

It will be appreciated that the probe functions in at least a dual capacity depending upon which ear is being monitored for intraaural muscle reflex. When the ear in which the probe lies is to be monitored for intraaural muscle reflex, tones are emanated from the send transducer 46 and are monitored by the receive 48 transducer with any necessary corrections in chamber pressure being made by the air pressure conduit 44. When the intraaural muscle reflex occurs, muscles in the inner ear cause the eardrum 76 to move from its position of maximum compliance which response may be detected as a change in pressure in chamber 116. Thus, the probe functions to maintain the eardrum in a condition of maximum compliance. On the other hand, when the ear into which the probe is inserted is the ear being audiologically stimulated in order to affect the muscular reflex in the opposite ear, the probe is functioning as an audio stimulus generator whereby tones of various frequencies and at carefully controlled amplitude are introduced for the purpose of eliciting contralateral muscular reflex.

When it is desired to remove the apparatus from the head of the patient, the pressure in the inflatable probe tip 70 may be released by opening the pump bulb valve 74 for both the left and right probes. The procedure for positioning the apparatus may be reversed, and the equipment may be readily removed.

SUMMARY OF ADVANTAGES AND SCOPE OF THE INVENTION

It will be appreciated that in constructing a novel audiometric device according to the present invention, certain significant advantages are provided. In particular, the auditory canals of both ears of a patient may be quickly probed with the apparatus of the present invention. After this initial probe operation, contralateral testing of intraaural muscular reflex may be performed on one ear and then the other without the necessity of having to remove a probe from the reflex ear and re-establish control conditions and without having to remove a muff type earphone and re-position it on another ear. In addition, the probe tip of the probes of the present invention may be readily replaced between patients. The apparatus of the present invention advantageously provides a disposable inflatable probe tip which assures a consistently satisfactory seal between the probe and the walls of the auditory canal.

By utilizing a probe simultaneously in both auditory canals, a physician or audiologist may achieve improved results in controlling the audiological parameters of a stimulus tone introduced into an ear being tested. Moreover, contralateral testing may be performed much more quickly and accurately than with prior art arrangements.

Additional advantages will be realized in the practice of the present invention by the virtually infinite adjustability of the probe. Axial and radial alignment may be more readily achieved with the arrangement disclosed with substantial savings in time and effort. In addition, the frame or carriage of the audiometric apparatus of the present invention may accomodate probe tips other than the inflatable type. For example, conical, noninflating probe tips may be utilized and may be biased inwardly into the auditory canal by adjustments in the horizontal slide rods of the vertical portions of the headset of the present invention.

Another advantageous feature of the present invention is the axial orientation of the probe in the auditory canal which is achieved when the inflatable probe tip is inflated. The probe tip has a tendency to axially align the probe with the longitudinal axis of that portion of the auditory canal wherein the probe lies.

Thus, it is apparent that there has been provided, in accordance with the invention, an audiometric headset that substantially satisfies the objects and advantages set forth above. Although the present invention has been described in conjunction with specific forms thereof, it is evident that many alternatives, modifications, and variations will be apparent to those skilled in the art in light of the foregoing disclosure of the invention. Accordingly, it is intended that all such alternatives, modifications, and variations fall within the spirit and scope of the invention as defined in the appended claims be embraced thereby.

What is claimed is:

1. Apparatus for sequenced contralateral testing of intraaural muscle reflex, said apparatus comprising:
   first probe means sealingly positionable in a first auditory canal of a patient for isolating a first volume therein;
   first inflatable bladder means carried by said first probe means for circumferentially expanding when pressurized fluid is introduced into said first bladder means;

said first probe means being operable to carry:

first pressure control means for controlling a pressure in the first volume;

first audio stimulus generating means for selectively producing an audio stimulus in the first auditory canal;

first response detecting means for detecting in the first auditory canal a response to the stimulus of said first audio stimulus generating means;

second probe means operably connectable to said first probe means, said second probe means being positionable in a second auditory canal of a patient for isolating a second volume therein;

second inflatable bladder means carried by said second probe means for circumferentially expanding when pressurized fluid is introduced into said second bladder means;

said second probe means being operable to carry:

second pressure control means for controlling a pressure in the second volume;

second audio stimulus generating means for selectively producing an audio stimulus in the second auditory canal;

second response detecting means for detecting in the second auditory canal a response to the stimulus of said second audio stimulus generating means;

said first pressure control means, said first audio stimulus generating means, and said first response detecting means being cooperable to displace an eardrum in the first auditory canal to a position having a first predetermined compliance;

said second audio stimulus means carried by said second probe means being operable when the first predetermined compliance is achieved to stimulate the eardrum in the second auditory canal and produce a reflex in the eardrum in the first auditory canal, said first pressure control means being operably responsive to the reflex of the first eardrum;

said second pressure control means, said second audio stimulus generating means, and said second response detecting means being cooperable to displace an eardrum in the second auditory canal to a position having a second predetermined compliance;

said first audio stimulus means carried by said first probe means being operable when the second predetermined compliance is achieved to simulate the eardrum in the first auditory canal and produce a reflex in the eardrum in the second auditory canal, said second pressure control means being operably responsive to the reflex of the second eardrum.

2. The audiometric apparatus of claim 1 and further comprising:

pivot means for pivotally supporting said first and second probe means to provide a range of substantially infinite radial positions for said first and second probe means; and axial support means for axially supporting said first and second probe means at a predetermined axial position, said pivot means and said axial support means being cooperable to facilitate insertion of said first and second probe means into auditory canals of varying geometry.

\* \* \* \* \*